United States Patent
Hofmann (10) Patent No.: US 9,795,355 B2
(45) Date of Patent: Oct. 24, 2017

(54) MULTI-CYCLE DYNAMIC CT IMAGING

(71) Applicant: Christian Hofmann, Erlangen (DE)

(72) Inventor: Christian Hofmann, Erlangen (DE)

(73) Assignee: Siemens Aktiengesellschaft, München (DE)

( * ) Notice: Subject to any disclaimer, the term of this patent is extended or adjusted under 35 U.S.C. 154(b) by 14 days.

(21) Appl. No.: 15/095,044

(22) Filed: Apr. 9, 2016

(65) Prior Publication Data

US 2016/0296193 A1 Oct. 13, 2016

(30) Foreign Application Priority Data

Apr. 9, 2015 (DE) .................... 10 2015 206 362

(51) Int. Cl.
*G06K 9/00* (2006.01)
*A61B 6/00* (2006.01)
*A61B 6/03* (2006.01)
*G06T 11/00* (2006.01)

(52) U.S. Cl.
CPC .............. *A61B 6/5288* (2013.01); *A61B 6/03* (2013.01); *A61B 6/032* (2013.01); *A61B 6/541* (2013.01); *G06T 11/00* (2013.01)

(58) Field of Classification Search
None
See application file for complete search history.

(56) References Cited

U.S. PATENT DOCUMENTS

| | | | | |
|---|---|---|---|---|
| 7,769,430 B2 * | 8/2010 | Mostafavi | ............ | A61B 5/1135 378/8 |
| 8,571,639 B2 * | 10/2013 | Mostafavi | .............. | A61B 6/504 378/65 |
| 8,788,020 B2 * | 7/2014 | Mostafavi | .............. | A61B 5/113 324/309 |

(Continued)

FOREIGN PATENT DOCUMENTS

DE  102006014625 B3  10/2007
WO  WO2015122687 A1  8/2015

OTHER PUBLICATIONS

Ford et al (Respiration correlated spiral CT: A method of masuring respiratory-induced anatomic motion for radiation, Medical physics 30, 88 (2003)).*

(Continued)

*Primary Examiner* — Shervin Nakhjavan
(74) *Attorney, Agent, or Firm* — Lempia Summerfield Katz LLC (57) ABSTRACT

A dynamic CT imaging method is provided. With the method, projection measurement data for a region of an examination object to be imaged is captured, with simultaneous correlated capture of the respiratory movement of the examination object. A phase of the respiratory movement, for which image data is to be reconstructed, is selected. Phase projection measurement data assigned to the selected phase is also determined. Transition regions of partial images of the region to be imaged between successive respiratory cycles are then reconstructed on a trial basis (Continued)

based on a part of the phase projection measurement data, and a standard reconstruction is performed using parts of the phase projection measurement data for each of the successive respiratory cycles assigned to an optimum reconstruction.

15 Claims, 4 Drawing Sheets

(56) References Cited

U.S. PATENT DOCUMENTS

| | | | |
|---|---|---|---|
| 2004/0125908 A1* | 7/2004 | Cesmeli | A61B 6/032 378/4 |
| 2007/0232888 A1 | 10/2007 | Bruder et al. | |
| 2011/0275933 A1* | 11/2011 | Dey | A61B 6/037 600/428 |
| 2012/0245453 A1* | 9/2012 | Tryggestad | A61B 6/463 600/413 |
| 2012/0278055 A1* | 11/2012 | Schweizer | A61B 6/037 703/11 |
| 2014/0072194 A1* | 3/2014 | Hansis | A61B 6/032 382/128 |

OTHER PUBLICATIONS

German Office action for related German Application No. 10 2015 206 362.3, dated Nov. 19, 2015, with English Translation.

Matthias Guckenberger et al., "Influence of retrospective sorting on image quality in respiratory correlated computed tomography", Radiotherapy and Oncology, vol. 85, pp. 223-231, www.thegreenjournal.com, 2007.

* cited by examiner

MULTI-CYCLE DYNAMIC CT IMAGING

This application claims the benefit of DE 10 2015 206 362.3, filed on Apr. 9, 2015, which is hereby incorporated by reference in its entirety.

BACKGROUND

The present embodiments relate to dynamic CT imaging.

Modern imaging methods are frequently used to generate two-dimensional or three-dimensional image data that may be used to visualize an imaged examination object and additionally for further applications.

The imaging methods are frequently based on the detection of x-ray radiation, with projection measurement data being generated. Projection measurement data may be acquired, for example, with the aid of a computed tomography system (CT system). With CT systems, a combination of x-ray source and opposing x-ray detector arranged on a gantry travels around a measurement space, in which the examination object (e.g., the patient) is located. The rotation center (e.g., the isocenter) corresponds, for example, to a system axis z. During the course of one or more circuits, the patient is irradiated with x-ray radiation from the x-ray source, with projection measurement data or x-ray projection data being captured with the aid of the opposing x-ray detector.

The generated projection measurement data (e.g., projection data) is a function, for example, of the model of x-ray detector. X-ray detectors may have a plurality of detection units (e.g., arranged in the form of a regular pixel array). The detection units each generate a detection signal for x-ray radiation striking the detection units. The detection signal is analyzed at defined time points with respect to intensity and spectral distribution of the x-ray radiation in order to provide information about the examination object and generate projection measurement data.

Reconstructed three-dimensional CT volumes are routinely used when planning radiation therapy for patients with lung and abdominal carcinomas. In order to be able to reconstruct the anatomy of a patient in a defined phase, a respiratory surrogate is used in synchronicity with the raw data acquisition in order to be able to establish a correlation between raw data and patient respiration. There are different options for radiation planning. A number of phases covering the entire respiratory cycle may be reconstructed. Such a reconstruction is also referred to as four-dimensional CT imaging. This is used to localize the movement of tumors and tissue at risk over the respiratory cycle to keep the planning target volume PTV as small as possible, thereby reducing the radiation exposure of the patient to be treated as far as possible. The accuracy of such planning is a function of the image quality of the 4D CT reconstructions. These are, however, very frequently impaired by 4D artifacts, as the external respiratory surrogate only reproduces the internal anatomy to a limited degree.

SUMMARY AND DESCRIPTION

The scope of the present invention is defined solely by the appended claims and is not affected to any degree by the statements within this summary.

It is desirable to reduce artifacts in order to provide the best possible radiation planning. The present embodiments may obviate one or more of the drawbacks or limitations in the related art. For example, image data with reduced 4D artifacts is generated during dynamic imaging.

With a dynamic CT imaging method of one or more of the present embodiments, projection measurement data is captured for a region of an examination object to be imaged. During acquisition of the projection measurement data, respiratory movement of the examination object is captured simultaneously in a correlated manner. The respiratory movement may be captured, for example, with the aid of a respiratory surrogate. This is an observation system (e.g., a camera system or a respiration monitoring belt) that is fitted with sensors and connected to a sensor signal detection-system. After the acquisition of the projection measurement data and the temporally correlated capture of the respiratory movement, a phase of the respiratory movement, for which image data is to be reconstructed, is selected. A phase of the respiratory movement generally refers to a time segment that recurs periodically during each respiratory cycle and is assigned to a state of the breathing examination object that is repeated during each respiratory cycle. The determination of one or more phases may take place based on the captured respiratory movement.

After phase selection, the projection measurement data assigned to the selected phase (e.g., phase projection measurement data) is determined. The position or start position of the corresponding projection measurement data may be calculated, for example, based on the quotient of the time points assigned to the selected phase and the overall acquisition time for the acquisition of the projection measurement data. A projection measurement data interval that includes the determined start position and corresponds to the assigned projection measurement data is then determined in each instance. For example, the projection measurement data interval may follow the start-position (e.g., the start position is at the left edge of the projection measurement data interval).

During the further course of the dynamic CT imaging method of one or more of the present embodiments, transition regions of subregions of the region to be imaged between successive respiratory cycles are reconstructed a number of times based on a plurality of different projection measurement data sets that correspond to different segments of the determined projection measurement data interval. The reconstruction of a transition region refers to the reconstruction of image data based on projection measurement data captured in successive respiratory cycles. The reconstructed image data includes, for example, a transition region that shows the transition between the image data of different respiratory cycles. The projection measurement data assigned to the respective respiratory cycles is acquired in a time interval of a respiratory cycle. However, as the reproduction of the respiratory cycle is generally imprecise, artifacts (e.g., step-type structures) generally occur in the transition regions.

During the multiple reconstruction of transition regions of subregions of the region to be imaged between successive respiratory cycles of the respiratory movement, candidate projection measurement data sets that are part of the phase projection measurement data are used.

The optimum reconstruction (e.g., the reconstruction with the fewest artifacts) is selected in each instance from the plurality of reconstructions for each of the transition regions. The candidate projection measurement data sets corresponding to an optimum reconstruction are determined as target projection measurement data here.

A standard reconstruction is performed using the projection measurement data sets assigned to the optimum reconstructions (e.g., the target projection measurement data for each of the successive respiratory cycles). Such target projection measurement data forms parts or subsets of the phase projection measurement data assigned to the selected phase. The standard reconstruction may include, for example, a standard WFBP reconstruction. This type of reconstruction of image data is based on a weighted filtered back projection WFBP.

The method of one or more of the present embodiments reduces 4D artifacts in CT reconstructions. This happens in a phase-specific manner in that prior knowledge of the different respiratory phases acquired with the aid of the external respiratory surrogate is also incorporated in the artifact reduction algorithm in order to provide the stability of the algorithm and to achieve maximum artifact reduction. As the optimization process of the method may take place before the final reconstruction, the optimization process allows the option of free phase selection.

The image data reconstruction facility of one or more of the present embodiments includes an input interface for capturing projection measurement data of a region of an examination object to be imaged with simultaneous correlated capture of the respiratory movement of the examination object. The image data reconstruction facility includes a selection unit for capturing selection information relating to a selected phase of the respiratory movement, for which image data is to be reconstructed. The image data reconstruction facility has a phase projection measurement data determination unit for determining the projection measurement data assigned to the selected phase. The image data reconstruction facility also includes a reconstruction unit for the multiple reconstruction of transition regions of subregions of the region to be imaged between successive respiratory cycles based on a part of the phase projection measurement data that forms candidate projection measurement data sets. The image data reconstruction facility includes a target projection measurement data determination unit for determining as target projection measurement data the candidate projection measurement data sets that correspond to an optimum reconstruction. The reconstruction unit is, for example, set up (e.g., configured) to perform a standard reconstruction using the target projection measurement data for each of the successive respiratory cycles.

The computed tomography system includes the image data reconstruction facility.

The majority of the essential components of the image data reconstruction facility may be configured in the form of software components or hardware components (e.g., a processor). This is the case, for example, for the phase projection measurement data determination unit and the reconstruction unit.

Some of the components (e.g., when particularly fast calculations are to be provided) may be in the form of software-assisted hardware (e.g., FPGAs or the like). Similarly, the interfaces may be configured as software interfaces (e.g., when it is simply a matter of transferring data from other software components). The interfaces may, however, also be configured as interfaces constructed from hardware, which are activated by appropriate software.

For example, the image data reconstruction facility may be part of a user terminal or a controller of a CT system.

A primarily software-based model has the advantage that control facilities that have already been used to date may also easily be upgraded by a software update in order to operate in the manner of one or more of the present embodiments. In one embodiment, a corresponding computer program product with a computer program that may be loaded directly into a storage facility of a control facility of a computed tomography system, with program segments for executing all the acts of the method when the program is run in the control facility, is provided. Such a computer program product may optionally include additional components such as, for example, documentation and/or additional components as well as hardware components, such as hardware keys (e.g., dongles, etc.) for the use of the software, in addition to the computer program.

A computer-readable medium (e.g., non-transitory; a memory stick, a hard drive or some other transportable or permanently built-in data carrier), on which the program segments of the computer program that may be read and executed by a computer unit of the control facility are stored, may be used for transfer to the control facility and/or for storage on or in the control facility. The computer unit may, for example, have one or more cooperating microprocessors or the like for this purpose.

One category may also be developed in the same way as another claim category. Also, the various features of different exemplary embodiments may also be combined to give new exemplary embodiments within the context of the present embodiments.

In one embodiment of the method, a start projection index interval assigned to the assigned phase projection measurement data is determined during the determination of the phase projection measurement data assigned to the selected phase, and a plurality of different candidate start projection indices are determined for each start projection index interval. Also, during the act of reconstructing transition regions between successive respiratory cycles based on a part of the phase projection measurement data, the multiple reconstruction may be started with the determined different candidate start projection indices.

The captured projection measurement data is generally indexed or stored indexed, and start projection indices corresponding to the selected phase are sought for each of the respiratory cycles. Such start projection indices indicate the position in the captured projection measurement data set at which the projection data for the selected phase starts or from which position the projection data may be read out for each of the respiratory cycles. Because the acquisition of the respiratory movement is temporally correlated, only the acquisition time point corresponding to one phase and the projection index of the projection measurement data corresponding to a defined acquisition time point are to be determined. Each projection measurement data set is assigned a projection index, to which a defined acquisition time point also corresponds. During constant acquisition, the respective start projection indices corresponding to a phase simply result from the total number of projection measurement data sets multiplied by the quotient of the acquisition time point assigned to a respective phase and the overall acquisition time. However, synchronization with the respiratory movement during acquisition is not perfect, so the projection measurement data assigned to the determined start projection indices does not always match up precisely (e.g., in the transition regions); this may result in the 4D artifacts mentioned above.

According to one or more of the present embodiments, a start projection index interval and candidate values for any matching start projection indices, the candidate start projection indices, are now determined around the start projection indices in the start projection index interval for each cycle. Test reconstructions for the transition regions between the respiratory cycles are performed based on the candidate values for the start projection indices.

Initially, the two facing edge segments of the reconstructed partial images assigned to the individual respiratory cycles do not match one another precisely in the transition regions (e.g., the two facing edge segments are displaced slightly in the horizontal direction). The adjacent edge segments are assigned to successive respiratory cycles and belong to first and second subregions or the partial images to be reconstructed and corresponding thereto. The individual subregions and corresponding partial images are, for example, each assigned to the same selected phase, and the partial images together form an overall image assigned to the phase.

At the projection measurement data level, the transition regions therefore correspond to the transition from the reconstruction of a set of projection measurement data assigned to a first respiratory cycle to the reconstruction of a set of projection measurement data assigned to a second respiratory cycle or a set of projection measurement data assigned to a respiratory cycle directly following a respiratory cycle.

When test reconstructions have been performed for the candidate values of the start projection indices, the test reconstructions are used to find optimum reconstructions with minimal artifacts, and the actual final reconstruction is performed with the aid of the projection measurement data assigned to the optimum test reconstructions.

In one embodiment of the method, optimum start projection indices are determined for the optimum reconstruction. The optimum start projection indices include the start projection indices for which the reconstructed transition regions between successive respiratory cycles match one another best. The criterion for how closely reconstructed transition regions between successive respiratory cycles match one another may be calculated in each instance as a displacement value of an artifact metric. The metric describing the artifact and the progression of the method may be configured such that the metric describing the artifact and the progression of the method may be used both for spiral acquisition protocols and for sequential acquisition protocols.

In one effective embodiment of the method that is particularly simple to implement, the respective start projection indices of the test reconstructions, for which the displacement value of the artifact metric is a minimum, are determined as the optimum start projection indices.

In one embodiment of the method, the standard reconstruction (e.g., a standard WFBP reconstruction) is performed using the determined optimum start projection indices for a plurality of different phases. For example, these different phases may include the phase of maximum inhalation and the phase of maximum exhalation.

In one variant of the method, the selection of a phase also includes the determination of the corresponding phase time points.

With the method, start projection indices that are assigned to a plurality of successive respiratory movement cycles and correspond to the selected phase time points may be determined with the aid of a binning method. Such a binning method is described in Matthias Guckenberger et al. "Influence of retrospective sorting on image quality in respiratory correlated computed tomography," Radiotherapy and Oncology 85 (2007) 223-231 www.thegreenjournal.com.

The start projection index intervals may also each be determined as an interval around the determined start projection indices. For example, the start projection indices may be located precisely in the center of a start projection index interval.

In one variant of the method, the multiple reconstruction of transition regions between successive respiratory cycles takes place with interpolation-free assignment to the respective respiratory cycle.

Interpolation-free assignment provides that there is no interpolation between data regions when data regions from more than one respiratory cycle are available for a z position.

The multiple reconstruction of transition regions between successive respiratory cycles may be performed sequentially for each of the successive respiratory cycles, starting with the first respiratory cycle that is part of the reconstruction, up to the last respiratory cycle.

In one specific embodiment of the method, freely selectable parameters are adapted in a phase-specific manner with the aid of the simultaneous correlated capture of the respiratory movement of the examination object. This provides that the different phases (e.g., to be reconstructed) are parameterized separately. For example, the phase of maximum inhalation and the phase of maximum exhalation are treated separately. One exemplary parameter would be the search width of the artifact reduction algorithm.

In an alternative embodiment of the method, a region in which artifacts are reduced is determined based on a previously performed conventional respiration-correlated image data reconstruction, and the method is performed for the determined region. The possibility of specifying a region of interest (ROI) (e.g., region to be imaged, a tumor volume) that is of particular importance for further radiation planning allows the artifact reduction method to be optimized specifically for the region.

DETAILED DESCRIPTION

Figure 1:
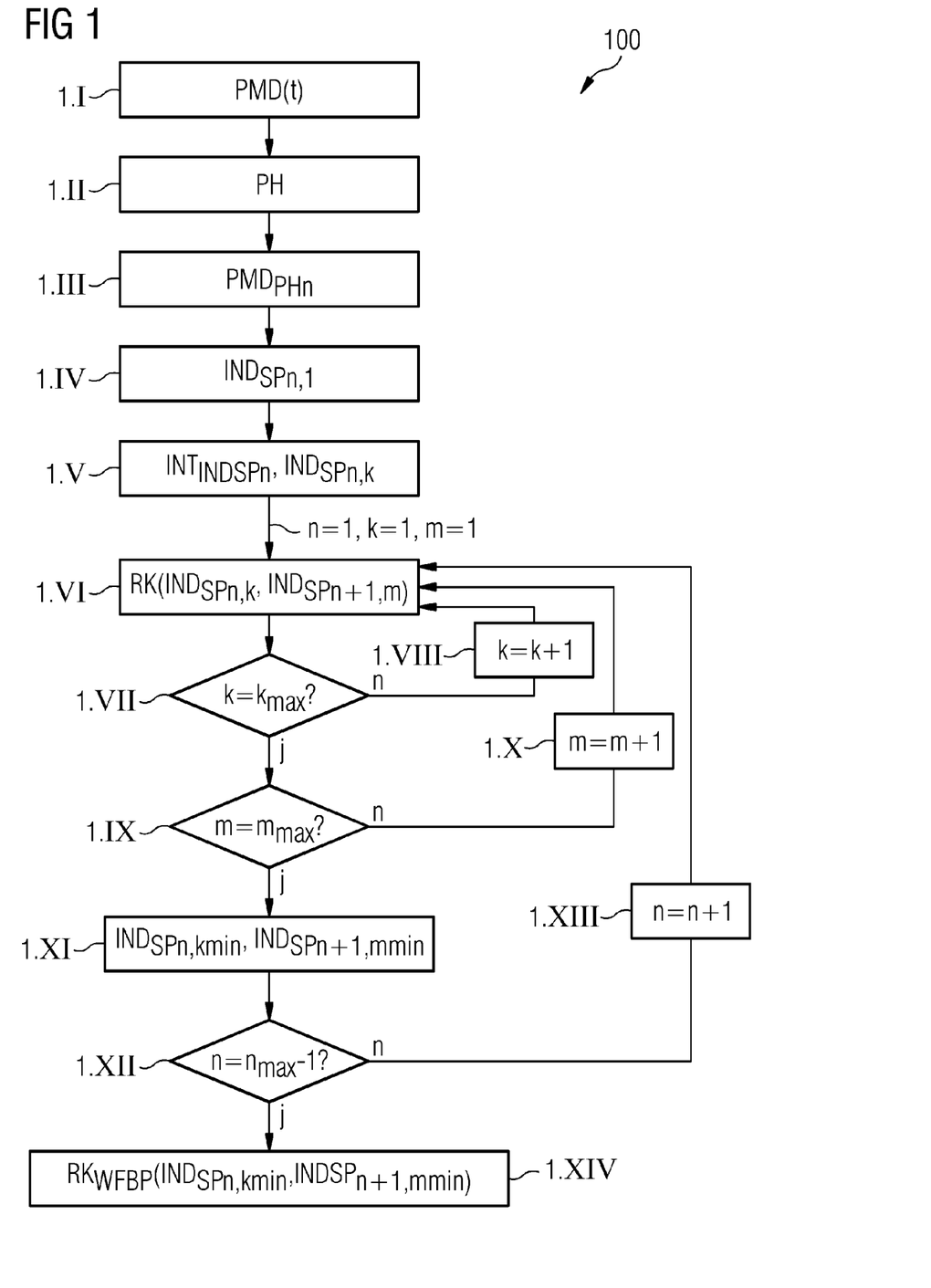
FIG. 1 shows a flow diagram illustrating an imaging method according to a first exemplary embodiment.

FIG. 1 shows a dynamic CT imaging method 100 according to an exemplary embodiment.

In act 1.I, raw data is acquired with the aid of an external respiratory surrogate. The respiratory surrogate may be implemented with the aid of a respiration monitoring system (e.g., a camera or respiration belt). Use of the respiratory surrogate serves to provide a first correlation between a respiratory phase PH to be reconstructed (see FIG. 2) and the acquired raw data PMD(t), also referred to as projection measurement data.

In act 1.II, the phases PH to be reconstructed are selected, for example, by a user. In other words, the phase PH of the respiratory cycle for which image data is to be generated is determined. In act 1.III, the projections or projection measurement data sets to be used for the selected phase are selected from the captured projection measurement data PMD(t) using an algorithm (e.g., a predefined binning algorithm). There are various binning algorithms, which are known in the literature as "phase-based", "local amplitude-based" or "global amplitude-based". Any of these approaches may be used for the described method. In act 1.IV, the start projection indices $IND_{SPn,1}$ for each respiratory cycle $Z_n$ corresponding to the selected projections or projection measurement data sets are identified. Also in act 1.V, the algorithm is used to determine a start projection index interval $INT_{INDSPn}$ around the respective start projection index $IND_{SPn,1}$ in a respiratory-cycle-specific manner.

In acts 1.VI to 1.XIV, a sequential search is performed for the optimum selection of start projection indices $IND_{SPn,k}$, $IND_{SPn+1,m}$ within permitted adjacent start projection index intervals $INT_{INDSPn}$, $INT_{INDSPn+1}$ of successive respiratory cycles. The aim is to find start projection indices $IND_{SPn,kmin}$, $IND_{SPn+1,mmin}$ (binning points) and thus projection measurement data sets for the final reconstruction $RK_{WFBP}(IND_{SPn,kmin}, IND_{SPn+1,mmin})$ in act 1.XIV, so that this final reconstruction has minimal artifacts.

More specifically in act 1.VI, the transition region between two respiratory cycles is reconstructed without overlap (e.g., with unambiguous interpolation-free assignment to the respective respiratory cycle) for a first start projection index $IND_{SP1,1}$ and the following start projection index $IND_{SP2,1}$ for the next respiratory cycle (this process is shown in FIG. 1 as $RK(IND_{SPn,k}, IND_{SPn+1,m})$). Two such respiratory cycles $Z_1$, $Z_2$ are shown in a partial diagram 202 on the right in FIG. 2. The binning regions assigned to the start projection index intervals $INT_{INDSP1}$, $INT_{INDSP2}$ of the two respiratory cycles are also shown there as vertical bars. On the left of FIG. 2, there is also a partial diagram 201 showing image data for a reconstructed transition region 203 between the two respiratory cycles $Z_1$ and $Z_2$. When the start projection indices have been determined, it may be seen from the technical parameters of the imaging system and the basic conditions of an image acquisition, which include, for example, the slice thickness of the slices of the image acquisition and the width of the detector of the imaging system, up to which projection index reconstruction takes place from the respective start projection index for a respiratory cycle.

In act 1.VII, it is checked whether a predefined number $k_{max}$ of start projection indices $IND_{Sp1,k}$ has been generated for the first respiratory cycle and used for reconstruction in act 1.VI. If not, as shown in FIG. 1 by "n", in act 1.VIII, the running index k is increased by the value 1, and in act 1.VI, a reconstruction is performed with new start projection indices $IND_{SP1,2}$ or $IND_{SP2,2}$. If it is determined in act 1.VII that reconstructions have been performed for all $k=k_{max}$ predefined start projection indices of the first respiratory cycle $Z_1$ for the transition region 203 between the first two respiratory cycles $Z_1$ and $Z_2$, as shown in FIG. 1 by "y", it is asked in act 1.IX whether all the reconstructions have also been performed for all the $m=m_{max}$ start projection indices $IND_{SP2,m}$ of the second respiratory cycle. If this is not yet the case, as shown in FIG. 1 by "n", in act 1.X, a running index m is increased by the value 1, and in act 1.VI, a reconstruction is performed with correspondingly amended start projection indices. If it is determined in act 1.IX that all the reconstructions have been performed, as shown in FIG. 1 by "y", in act 1.XI, the optimum start projection indices $IND_{SP1,kmin}$, $IND_{SP2,mmin}$ are determined for the transition region 203 between the first two respiratory cycles $Z_1$ and $Z_2$. An artifact metric is calculated, which quantifies how closely the adjacent reconstructed slices from the two respiratory cycles $Z_1$, $Z_2$ match, and the transition with the smallest artifact metric value is selected (e.g., with the start projection indices $IND_{SP1,kmin}$, $IND_{SP2,mmin}$), the assigned reconstruction of which gives the smallest artifact—metric value. In act 1.XII, it is determined whether all the optimum start projection indices have been determined for all the $n=n_{max}$ respiratory cycles. If not, as shown in FIG. 1 by "n", in act 1.XIII, a running index n is increased by the value 1, and in act 1.VI, a reconstruction is performed again for the next transition region (e.g., between the second and third respiratory cycles $Z_2$, $Z_3$). Acts 1.VI to 1.XIII are also performed for each transition region between all successive respiratory cycles $Z_n$, $Z_{n+1}$. If it is determined in act 1.XII that the reconstructions have been performed for all the $n_{max}$-1 transition regions ($n_{max}$ is the number of respiratory cycles), in act 1.XIV, a standard WFBP reconstruction is performed for each phase PH to be reconstructed with the previously adapted binning points (e.g., the determined optimum start projection indices $IND_{SPn,kmin}$, $IND_{SPn,mmin}$). This reconstruction is shown as $RK_{WFBP}(IND_{SPn,kmin}, IND_{SPn+1,min})$ in FIG. 1.

The freely selectable parameters of the method 100 may be adjusted in a phase-specific manner, in that prior knowledge of the different respiratory phases acquired with the aid of the external respiratory surrogate is also incorporated. This serves to provide the stability of the algorithm and to achieve maximum artifact reduction.

Figure 2:
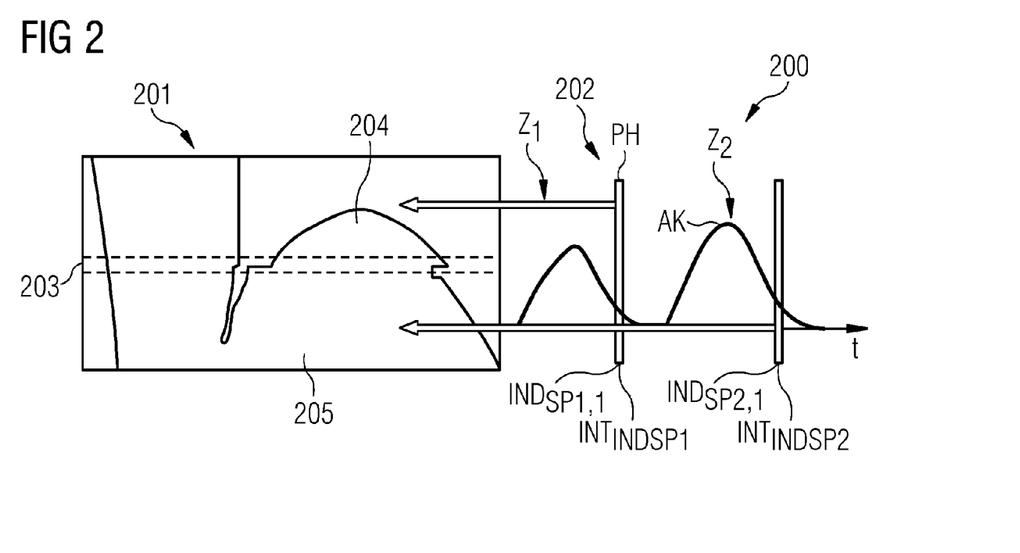
FIG. 2 shows a diagram illustrating an exemplary reconstruction of image data assigned to a selected phase.

The diagram 200 in FIG. 2, as mentioned above, shows a partial diagram 201 of a reconstruction based on projection measurement data for two respiratory cycles $Z_1$, $Z_2$. A partial diagram 202 on the right in FIG. 2, corresponding to the partial diagram 201 on the left showing the selected phase, shows corresponding binning regions as vertical bars in a respiratory curve AK. The binning regions are assigned start projection indices $IND_{SP1,1}$, $IND_{SP2,1}$. As described in relation to FIG. 1, start projection index intervals $INT_{INDSP1}$, $INT_{INDSP1}$ are also determined around the start projection indices $IND_{SP1,1}$, $IND_{SP2,1}$, in which further candidates for start projection indices may be set. The binning regions are assigned projection measurement data sets, from which in the method of one or more of the present embodiments, by selecting the matching candidates for the start projection indices, a subset of the projection measurement data sets, with which the reconstruction of partial images is finally performed to provide an overall image, is selected. The partial images have transition regions that only match closely when optimum start projection indices are selected.

To illustrate this problem, the partial diagram 201 shows a transition region 203 marked with a broken line between the two respiratory cycles $Z_1$ and $Z_2$. In this transition region, the two edge segments of the first and second subregions or partial images 204, 205 facing one another do not match precisely (e.g., the two edge segments are displaced slightly in the horizontal direction). The edge segments are assigned to a respective respiratory cycle $Z_1$, $Z_2$ and belong to first and second partial images 204, 205. The first and second partial images are, for example, each assigned to the same selected phase PH and together form the overall image 201.

Figure 3:
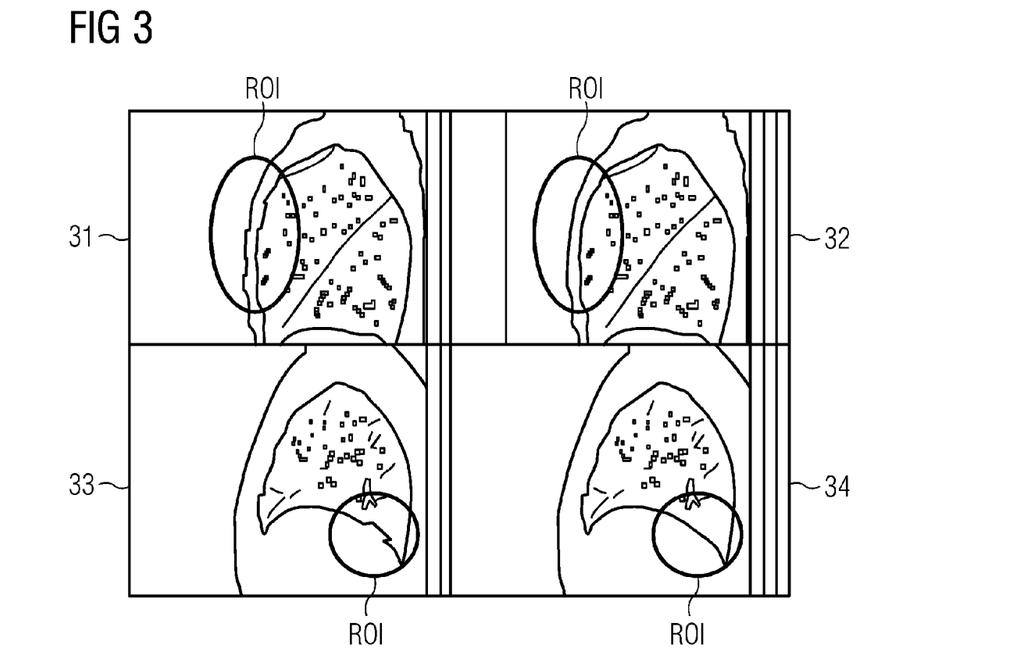
FIG. 3 shows a flow diagram illustrating a planning method according to an exemplary embodiment.

FIG. 3 shows a comparison between a conventional respiration-correlated 4D CT reconstruction without optimum selection of the binning points and an artifact-reduced 4D CT reconstruction according to an exemplary embodiment. The left-hand partial drawings 31, 33 each show the result of a conventional reconstruction, and by contrast, the right-hand partial drawings 32, 34 show image acquisitions performed with the aid of an artifact-reduced 4D CT reconstruction according to an exemplary embodiment. The left-hand partial drawings 31, 33 each show step-type artifacts within a subregion ROI, marked with a circular line. The artifacts are no longer present in the corresponding subregions ROI in the two right-hand partial drawings 32, 34.

Figure 4:
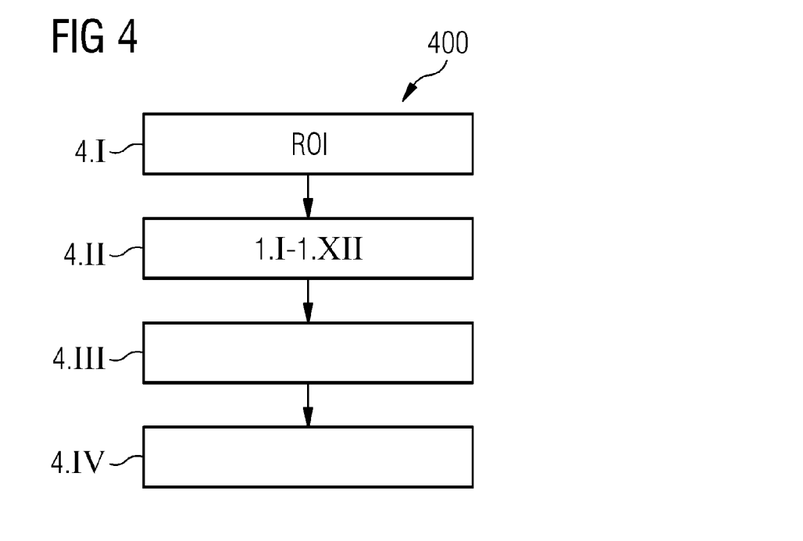
FIG. 4 shows representations of conventional image acquisitions and image acquisitions produced with the aid of a method according to an exemplary embodiment.

FIG. 4 shows one embodiment of a method 400 for performing radiation planning for a tumor. In act 4.I, a conventional respiration-correlated reconstruction is used to determine a region ROI of an examination object O, in which the tumor is located. In act 4.II, the method 100 is applied to the image of the tumor but the region to be imaged is limited to the region ROI determined in act 4.I. The image generated in act 4.I is supplemented in act 4.III by the image generated in act 4.II in the region ROI. In other words, the region ROI present in the conventional image is replaced by the image generated in act 4.II. In act 4.IV, radiation of the tumor is planned in synchronicity with the dynamic 4D image generated in act 4.III. For example, a corresponding protocol is produced, according to which subsequent dynamic imaging is performed.

Figure 5:
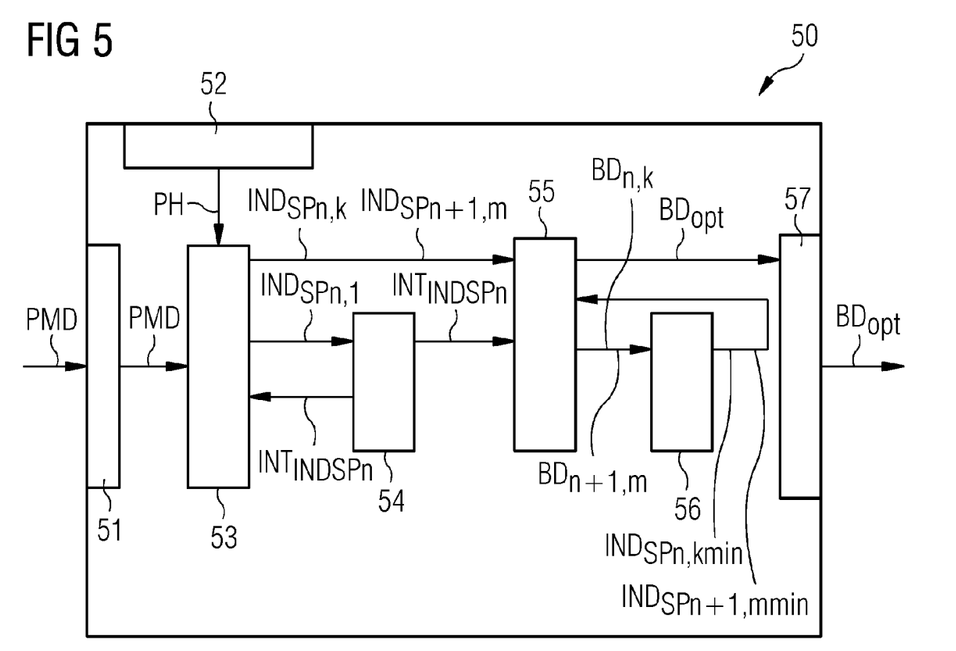
FIG. 5 shows a block diagram with an image data reconstruction facility according to an exemplary embodiment.

FIG. 5 shows a schematic diagram of an image data reconstruction facility 50 (e.g., an image data reconstruction device) according to an exemplary embodiment. The image data reconstruction facility 50 includes an input interface 51 that captures projection measurement data PMD(t) for a region VOI of an examination object O to be imaged (see FIG. 6). The projection measurement data PMD(t) is captured with the simultaneous correlated capture of the respiratory movement of the examination object O. The capture of the respiratory movement may be performed, for example, with the aid of a respiratory surrogate (see FIG. 6). A respiratory curve generated with the aid of the respiratory surrogate is then used to determine phases PH for which an image data determination or image data reconstruction is to be performed.

The selected phases PH are transferred to a selection unit 52 of the image data reconstruction facility 50, which receives such selection information relating to the selected phases PH of the respiratory movement, for which image data is to be reconstructed. Based on this information, a start projection index determination unit 53 determines a start projection index $IND_{SPn,1}$ for each of N respiratory cycles. A start projection index interval determination unit 54 then determines corresponding start projection index intervals $INT_{INDSPn}$ around the start projection indices $IND_{SPn,1}$, to which projection measurement data $PMD_{PHn}$, the projection indices of which are within the start projection index intervals $INT_{SPn}$, are assigned. Additional start projection indices $IND_{SPn,k}$, $INDP_{SPn+1,m}$, which are part of the start projection index intervals $INT_{ISPn}$, are also determined by the start projection index determination unit 53 based on the start projection index intervals $INT_{INDSPn}$ determined by the start projection index interval determination unit 54.

Based on the captured projection measurement data PMD and the start projection indices $IND_{SPn,k}$, $IND_{SPn+1,m}$ determined by the start projection index determination unit 53, to which candidate projection measurement data sets $PMD_K$ correspond in each instance, a reconstruction unit 55 reconstructs image data $BD_{n,k}$, $BD_{n+1,m}$ for each of the transition regions between successive respiratory cycles $Z_n$, $Z_{n+1}$. The image data $BD_{n,k}$, $BD_{n+1, m}$ is examined by a target projection measurement data determination unit 56 to determine which of the image data $BD_{n,mmin}$, $BD_{n+1,mmin}$ shows the smallest artifacts. The start projection indices $IND_{SPn,kmin}$, $IND_{SPn+1,mmin}$ assigned to the image data $BD_{n,kmin}$, $BD_{n+1,mmin}$, which correspond to assigned target projection measurement data $PMD_Z$, are then transferred to the reconstruction unit 55. The reconstruction unit 55 performs a standard WFBP reconstruction using the optimum start projection indices $IND_{SPn,kmin}$, $IND_{SPn+1,mmin}$ for each of the successive respiratory cycles $Z_n Z_{n+1}$, so that optimized image data $BD_{opt}$ is generated. The optimized image data $BD_{opt}$ determined during the reconstruction is transferred to an output interface 57, which forwards the image data $BD_{opt}$ to external units, such as storage units or terminals, for example.

Figure 6:
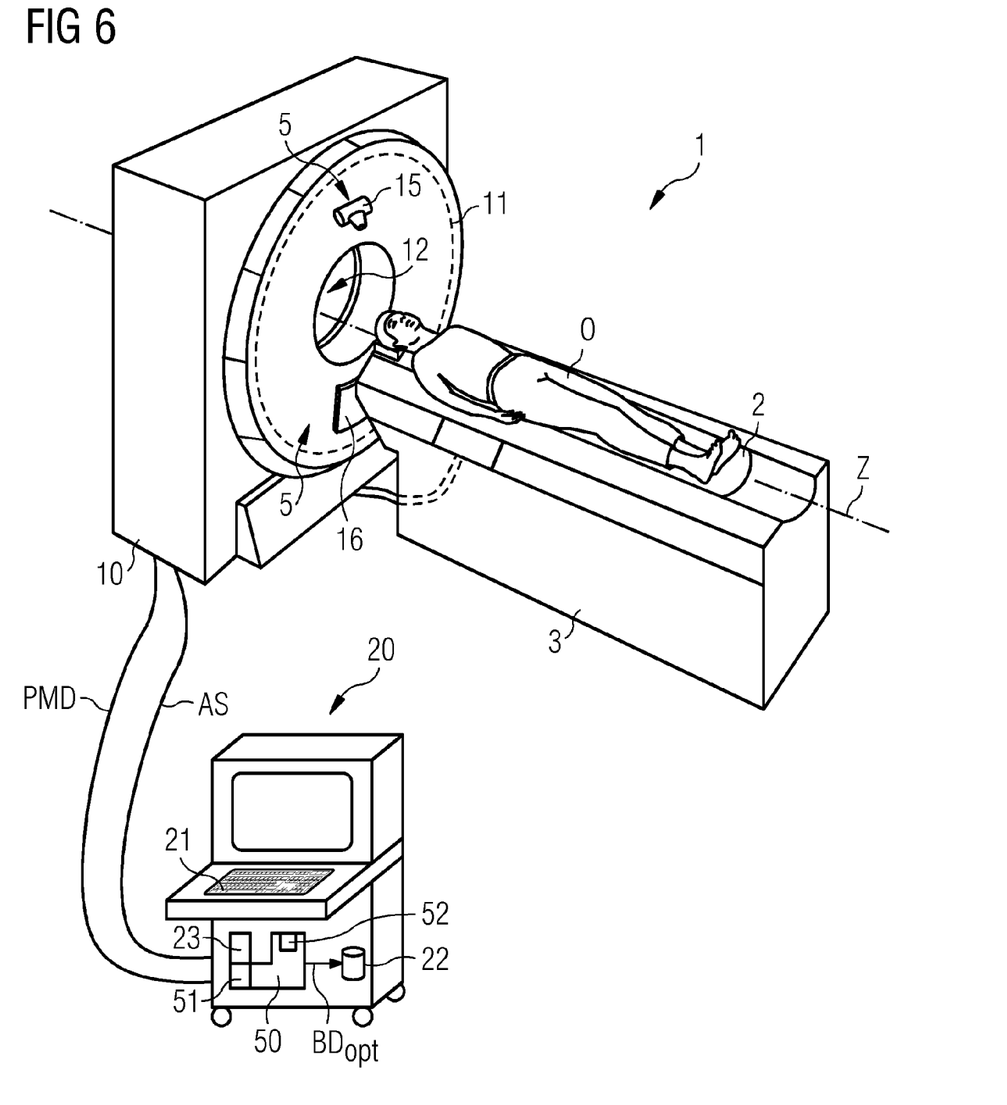
FIG. 6 shows a schematic representation of a computed tomography system according to an exemplary embodiment.

FIG. 6 shows a schematic diagram of a computed tomography system (CT system) 1 with one embodiment of an image data reconstruction facility 50.

The CT system 1 essentially includes a scanner 10, in which a projection data acquisition unit 5 with a detector 16 and an x-ray source 15 opposite the detector 16 travels around a measurement space 12 on a gantry 11. Located in front of the scanner 10 is a patient support facility 3 or patient table 3, the upper part 2 of which holds a patient O and may be moved together with the patient O toward the scanner 10 in order to move the patient O through the measurement space 12 relative to the detector system 16. The scanner 10 and patient table 3 are activated by a control facility 20, from which acquisition control signals AS are output via a standard control interface 23 to activate the entire system according to predefined measurement protocols in the conventional manner. The movement of the patient O along the z direction, which corresponds to the system axis z longitudinally through the measurement space 12, and the simultaneous circulation of the x-ray source 15 provide that the x-ray source 15 describes a helical path relative to the patient O during measurement. The detector 16 always runs in a parallel manner opposite the x-ray source 15 in order to capture projection measurement data PMD, which is then used to reconstruct volume and/or slice image data.

A sequential measuring method, in which a fixed position is approached in the z direction and during a circuit, a partial circuit or a number of circuits the required projection measurement data PMD is captured at the relevant z position, may also be performed in order to reconstruct a slice image at the z position or in order to reconstruct volume image data from the projection data from a number of z positions.

The method may also be used in principle on other CT systems (e.g., with a number of x-ray sources and/or detectors and/or with a detector forming a complete ring).

The projection measurement data PMD acquired by the detector 16 (also referred to in the following as raw data) is transferred via a raw data interface, which in this exemplary embodiment is the input interface 51 of the image data reconstruction facility 50, to the control facility 20 or the image data reconstruction facility 50 contained therein. The raw data is further processed in the manner described above in the image data reconstruction facility 50. In this exemplary embodiment, the image data reconstruction facility 50 is implemented in the form of software on a processor in the control facility 20.

After processing in the image data reconstruction facility 50, the determined image data $BD_{opt}$ is output to a storage unit 22 and, for example, to an output unit of the control facility 20 of the CT system.

Before image reconstruction, a respiratory curve generated with the aid of the respiratory surrogate is used to determine phases PH, for which an image data determination or image data reconstruction is to be performed.

The image data reconstruction facility 50 also includes, as mentioned above in relation to FIG. 5, a selection unit 52 that receives the selection information relating to the selected phases PH of the respiratory movement, for which image data is to be reconstructed, from an input unit 21 of the control facility 20.

The methods and devices described above are only exemplary embodiments, and the invention may be varied by the person skilled in the art without departing from the scope of the invention, as defined by the claims. The invention is not restricted to applications in the medical field but may also be used for the acquisition of CT images for other purposes. The use of the indefinite article "a" or "an" does not exclude the possibility of more than one of the relevant features being present. Similarly the term "unit" does not exclude the possibility of the present embodiments including a number of components that may also be distributed spatially.

The elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent. Such new combinations are to be understood as forming a part of the present specification.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A dynamic CT imaging method comprising:
   capturing projection measurement data for a region of an examination object to be imaged, with simultaneous correlated capture of respiratory movement of the examination object;
   selecting a phase of the respiratory movement, for which image data is to be reconstructed;
   determining phase projection measurement data assigned to the selected phase;
   multiple reconstructing transition regions of subregions of the region to be imaged between successive respiratory cycles of the respiratory movement based on candidate projection measurement data sets that are part of the phase projection measurement data;
   determining the candidate projection measurement data sets, which correspond to an optimum reconstruction, as target projection measurement data; and
   performing a standard reconstruction using the target projection measurement data for each of the successive respiratory cycles.

2. The method of claim 1, wherein the determining of the phase projection measurement data assigned to the selected phase comprises:
   determining at least one start projection index interval assigned to the assigned phase projection measurement data;
   determining a plurality of different candidate start projection indices for each start projection index interval; and
   performing the reconstruction of transition regions between successive respiratory cycles based on a part of the phase projection measurement data, the multiple reconstruction starting with the plurality of determined different candidate start projection indices.

3. The method of claim 2, further comprising determining, for optimum reconstruction, optimum start projection indices, the optimum start projection indices including the plurality of different candidate start projection indices, for which the reconstructed transition regions between successive respiratory cycles match one another best, calculating a criterion for how closely reconstructed transition regions between successive respiratory cycles match one another in each instance as a displacement value of an artifact metric, or a combination thereof.

4. The method of claim 3, wherein the respective candidate start projection indices, for which the displacement value of the artifact metric is a minimum, are determined as the optimum start projection indices.

5. The method of claim 2, wherein the standard reconstruction is performed using the determined optimum start projection indices for a plurality of different phases.

6. The method of claim 1, wherein selecting the phase comprises determining corresponding phase time points.

7. The method of claim 2, further comprising determining start projection indices that are assigned to a plurality of successive respiratory movement cycles and correspond to selected phase time points with the aid of a binning method.

8. The method of claim 7, further comprising determining each of the at least one start projection index interval as an interval around the determined start projection indices.

9. The method of claim 1, wherein the multiple reconstructing of transition regions between successive respiratory cycles is performed with interpolation-free assignment to the respective respiratory cycle.

10. The method of claim 1, wherein the multiple reconstructing of transition regions between successive respiratory cycles is performed sequentially for each of the successive respiratory cycles, starting with a first respiratory cycle that is part of the reconstruction, up to a last respiratory cycle.

11. The method of claim 1, wherein freely selectable parameters are adapted in a phase-specific manner with the aid of the simultaneous correlated capture of the respiratory movement of the examination object.

12. The method of claim 1, further comprising:
   determining a region in which artifacts are to be reduced based on a previously performed respiration-correlated standard image data reconstruction; and
   for the determined region in which artifacts are to be reduced:
      capturing projection measurement data with simultaneous correlated capture of respiratory movement of the examination object;
      selecting a phase of the respiratory movement, for which image data is to be reconstructed;
      determining phase projection measurement data assigned to the selected phase;
      multiple reconstructing transition regions of subregions between successive respiratory cycles of the respiratory movement based on candidate projection measurement data sets that are part of the phase projection measurement data;
      determining the candidate projection measurement data sets, which correspond to an optimum reconstruction, as target projection measurement data; and
      performing a standard reconstruction using the target projection measurement data for each of the successive respiratory cycles.

13. An image data reconstruction device comprising:
   an input interface configured to capture projection measurement data for a region of an examination object to be imaged, with simultaneous correlated capture of respiratory movement of the examination object;

a processor configured to:
  capture selection information relating to a selected phase of the respiratory movement, for which image data is to be reconstructed;
  determine the projection measurement data assigned to the selected phase;
  multiple reconstruct of transition regions of subregions of the region to be imaged between successive respiratory cycles based on candidate projection measurement data sets of a part of the phase projection measurement data;
  determine the candidate projection measurement data sets, which correspond to an optimum reconstruction, as target projection measurement data; and
  perform a standard reconstruction using the target projection measurement data for each of the successive respiratory cycles.

14. A computed tomography system comprising:
a control system comprising:
  an image data reconstruction device comprising:
    an input interface configured to capture projection measurement data for a region of an examination object to be imaged, with simultaneous correlated capture of respiratory movement of the examination object;
    a processor configured to:
      capture selection information relating to a selected phase of the respiratory movement, for which image data is to be reconstructed;
      determine the projection measurement data assigned to the selected phase;
      multiple reconstruct of transition regions of subregions of the region to be imaged between successive respiratory cycles based on candidate projection measurement data sets of a part of the phase projection measurement data;
      determine the candidate projection measurement data sets, which correspond to an optimum reconstruction, as target projection measurement data; and
      perform a standard reconstruction using the target projection measurement data for each of the successive respiratory cycles.

15. In a non-transitory computer-readable storage medium storing instructions executable by a computer for dynamic CT imaging, the instructions comprising:
  capturing projection measurement data for a region of an examination object to be imaged, with simultaneous correlated capture of respiratory movement of the examination object;
  selecting a phase of the respiratory movement, for which image data is to be reconstructed;
  determining phase projection measurement data assigned to the selected phase;
  multiple reconstructing transition regions of subregions of the region to be imaged between successive respiratory cycles of the respiratory movement based on candidate projection measurement data sets that are part of the phase projection measurement data;
  determining the candidate projection measurement data sets, which correspond to an optimum reconstruction, as target projection measurement data; and
  performing a standard reconstruction using the target projection measurement data for each of the successive respiratory cycles.

* * * * *